United States Patent [19]
Martel et al.

[11] 4,024,172
[45] May 17, 1977

[54] PREPARATION OF PROSTANOIC ACID DERIVATIVES

[75] Inventors: Jacques Martel, Bondy; Jean Buendia, Fontenay-sous-Bois; Edmond Toromanoff, Paris, all of France

[73] Assignee: Roussel-UCLAF, Paris, France

[22] Filed: Aug. 30, 1971

[21] Appl. No.: 176,234

[30] Foreign Application Priority Data

Sept. 4, 1970 France .............................. 70.32255
Nov. 30, 1970 France .............................. 70.42924

[52] U.S. Cl. .................. 260/468 D; 260/240 R; 260/410.9 R; 260/413; 260/514 D
[51] Int. Cl.² .................................. C07C 177/00
[58] Field of Search ................... 260/468 D, 514 D

[56] References Cited

UNITED STATES PATENTS 3,678,092   7/1972   Finch ............................... 260/468

OTHER PUBLICATIONS

Rapoport, J.A.C.S. 89, 1942 (1967).

House, Modern Synthetic Reactions, p. 139, (1964).
Fiesen et al., Reagents for Organic Synthesis pp. 189–190 (1967).

*Primary Examiner*—Robert Gerstl
*Attorney, Agent, or Firm*—Hammond & Littell

[57] ABSTRACT

A novel process for the preparation of derivatives of prostanoic acids of the prostaglandin $A_2$ ($PGA_2$) group of the formula

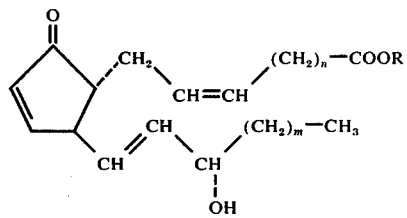

wherein R is selected from the group consisting of hydrogen and lower alkyl, $n$ is a whole number of 2, 3 or 4 and $m$ is a whole number of 3, 4 or 5 and to novel intermediates produced in the said process.

7 Claims, No Drawings

PREPARATION OF PROSTANOIC ACID DERIVATIVES

STATE OF THE ART

Prostaglandin $A_2$ ($PGA_2$) or 15α-hydroxy-9-oxo-5-cis,10,13-trans prostatrienoic acid or medulline is known to be isolated from renal medullar by extraction of the frozen medullar of rabbit kidneys. Prostaglandin $A_2$ is known to possess very interesting therapeutic properties, particularly hypotensive activity at very low doses. The said product appears to have a superior effectiveness when compared to ordinary vasodilators.

Attempts have been mde to synthesize prostaglandin $A_2$. Pike et al [Nobel Symposium 2, (1966), p. 161] describes dehydraton of prostaglandin $E_2$ with acetic acid to obtain $PGA_2$ but this process has various disadvantages. The yields are very low because the starting material is obtainable only by extraction of material originating from animals which is expensive and makes purification difficult and yields uncertain or by a total synthesis which require a number of complicated steps [Schneider, Chem. Com., Vol 6D (1969), p. 304]. Moreover, since synthesis steps are not always stereospecific, a mixture of isomers is often obtained requiring separation at one point in the synthesis or at the end thereof which separation procedures are difficult to effect on an industrial scale.

OBJECTS OF THE INVENTION

It is an object of the invention to provide a novel process for the preparation of the compounds of formula I in excellent yields without the prior art disadvantages.

It is a further object of the invention to provide novel intermediates for the preparation of the compounds of formula I.

These and other objects and advantages of the invention will become obvious from the following detailed description.

THE INVENTION

The novel process of the invention for the preparation of a compound of the formula

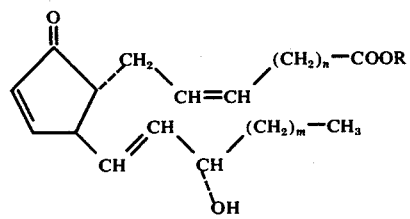

wherein R is selected from the group consisting of hydrogen and lower alkyl and $n$ is 2, 3 or 4 and $m$ is 3, 4 or 5 comprises reacting a compound of the formula

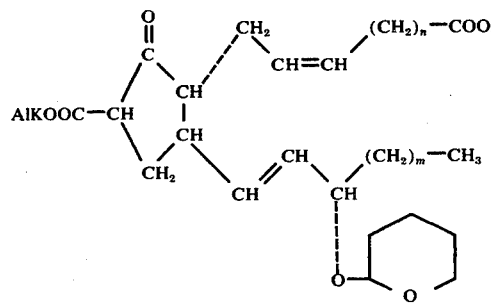

wherein AlK and $AlK^1$ are lower alkyl with a methylating agent to form a compound of the formula

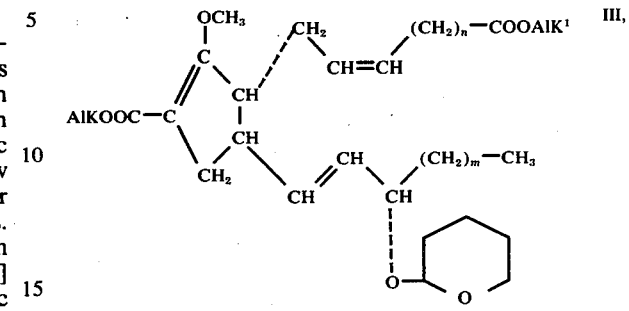

saponifying the said compound with a basic agent to form a compond of the formula

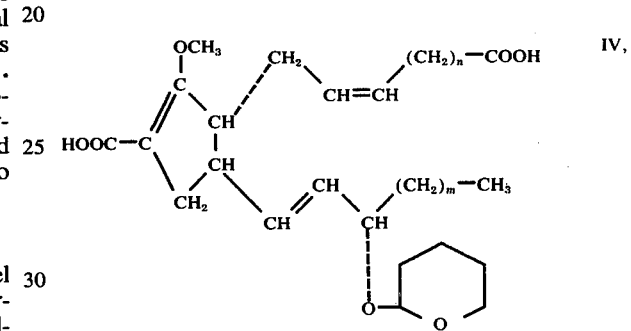

heating the said compound to form a compound of the formula

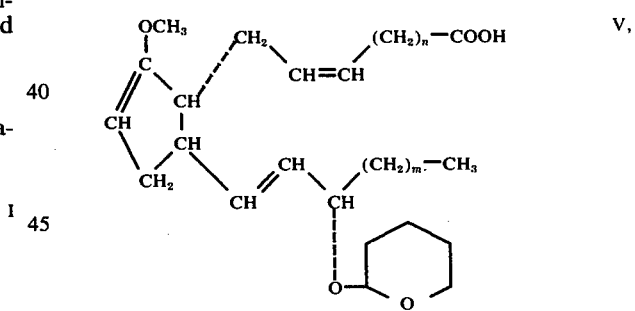

reacting the latter with an esterification agent to obtain an ester of the formula

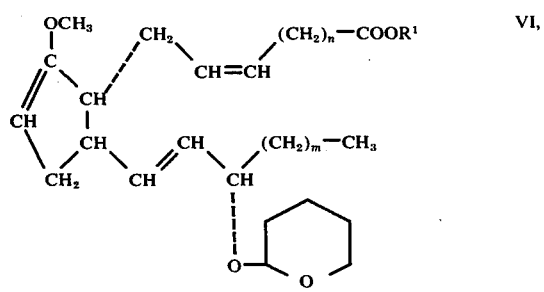

wherein $R^1$ is a lower alkyl, reacting the latter with bromine in a methanolic media to orm a bromo ketal of the formula

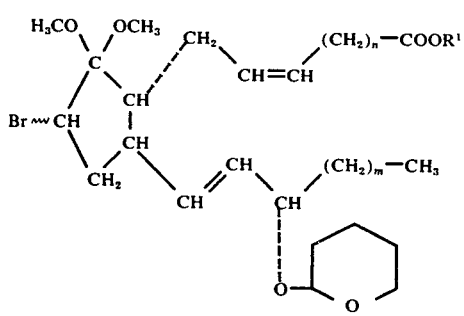

dehydrobrominating the latter with a dehydrobrmination agent to form a compound of the formula

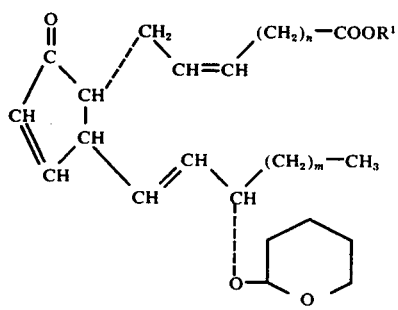

and subjecting the latter to acid hydrolysis to form the ester compound of formula I wherein R is lower alkyl which may be saponified with a mild base to the corresponding acid.

In a preferred embodiment of the process, the methylating agent is diazomethane. The saponification of the compound of formula III is preferably effected with an alkali metal hydroxide such as sodium hydroxide or potassium hydroxide at a temperature below 50° C. The heat treatment of the commpound of formula IV is preferably effected at 50° to 120° C in anhydrous organic solvent such as xylene.

The esterification agent to form the ester of formula VI is preferably a diazoalkane and the reaction is effected in an organic solvent such as methylene chloride, chloroform or dichloroethane. The ester may also be formed by reaction of the alkali metal, i.e. sodium or potassium, salt of the acid with an alkyl halide, i.e. iodide or bromide, or by reacting the acid with a dialkyl sulfate in the presence of a basic agent such as sodium bicarbonate. Other convenient esterification methods may be used such as esterification with a dialkyl ketal of dimethylformamide corresponding to the desired ester or formation of the methyl ester by reaction with methanol in the presence of the dimethyl ketal of acetone.

The selective bromo-methoxylation of the ester of formula VI may be effected under particularly mild conditions to avoid brominating the double bonds in the 5- and 13-positions and to avoid migration of the bromine. It is preferably effected with methanolic bromine at a temperature of −30° to −70° C and preferably in the presence of an alkali metal salt of a weak acid such as sodium acetate or disodium hydrogen phosphate.

The dehydrobromination agent for reaction with the compound of formula VII is preferably a diaza-bicycloalkene, particularly 1,5-diaza-bicyclo [4-3-O] nonene-5, and the reaction is effected in a dipolar aprotic solvent such as dimethylsulfoxide, dimethylformamide, dimethylacetamide and hexamethyl-phophortriamide. The acide hydrolysis of the compound of formula VIII is preferably effected with oxalic acid as the acid agent in a organic solvent such as ethanol. The saponification of the alkyl ester of formula I can be effected with a mild base such as sodium bicarbonate.

Certain of the reaction steps of the process can be effected without purification of the material from the preceding step. For example, the compound of formula IV can be heated to form the compound of formula V can be reacted without purification with an esterification agent.

The starting compounds of formula II can be prepared by the process of commonly assigned, copending application Ser. No. 138,276 filed Apr. 28, 1971 which comprises condensing alkyl 3-alkenyl-cyclopentanone-2-carboxylate of the formula

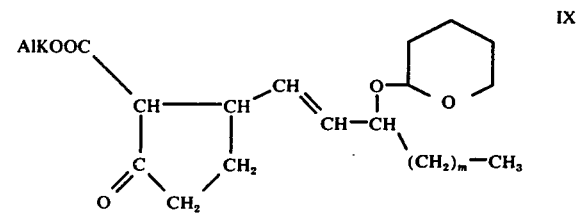

wherein AIK is lower alkyl and m is 3, 4 or 5 in the presence of an alkaline agent with an alkyl haloalkenoate of the formula

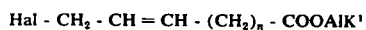

wherein Hal is chlorine or bromine, $AlK^1$ is lower alkyl and $n$ is 2,3 or 4 to form an alkyl carbalkoxy-prostadienoate of the formula

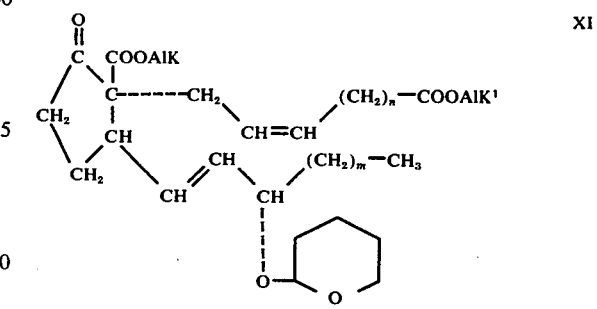

and reacting the latter with an alkali metal alcoholate to form a compound of the formula

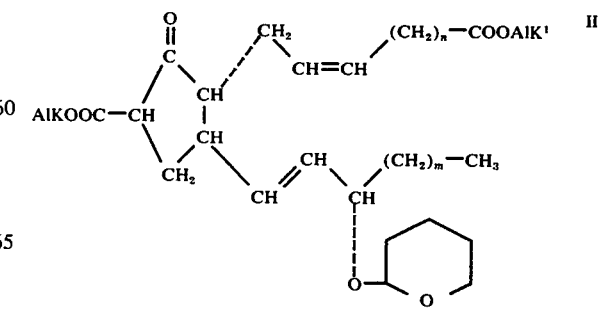

The alkyl haloalkeneoates of formula X may be prepared as described in copending, commonly assigned U.S. patent application Ser. No. 138,275 filed on Apr. 28, 1971 which comprises condensing a bromohaloalkane of the formula

Br - (CH$_2$)$_n$ - Hal'    XII wherein Hal' is bromine or chlorine and n is 2, 3 or 4 with tetrahydropyranyl ether of propargyl alcohol in the presence of an alkali metal in liquid ammonia to form (α-tetrahydropyranyloxy) haloalkyne of the formula

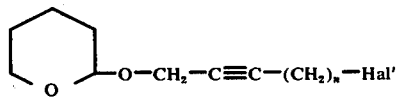

reacting the latter with an alkali metal cyanide followed by hydrolysis in a basis media to obtain α(tetrahydropyranyloxy) alkynoic acid of the formula

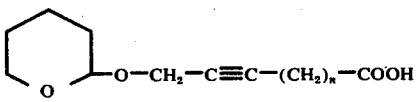

reacting the latter with an esterification agent to form the corresponding ester of the acid of formula XIV, hydrolyzing the said ester in an acid media to remove the α-tetrahydropyranyl group and hydrogenating the resulting alkyl hydroxyalkneoate in the presence of a partially deactivated catalyst to obtain a compound of the formula

HO-CH$_2$-CH=CH-(CH$_2$)$_n$ - COOAlK'   XV and reacting the latter with a halogenating agent to obtain the corresponding alkyl haloalkenoate of formula X. The alkyl 3-alkenyl-cyclopentanone-2-carboxylate of formula IX can be prepared as described in copending, commonly assigned application Ser. No. 138,274 filed on Apr. 28, 1971 by reacting propargylacetic acid or a derivative thereof with a precursor agent for alkyl acetate to form alkyl 3-oxo-6-heptyneoate of the formula

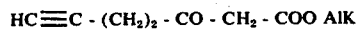
HC≡C - (CH$_2$)$_2$ - CO - CH$_2$ - COO AlK    XVI wherein AlK is lower alkyl, reacting the latter with an etherification agent to form alkyl 3-alkoxy-6-yne-2-hepteneoate of the formula

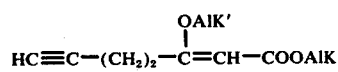

where AlK' is lower alkyl, condensing the latter in the form of a metallic salt with a α-halo-alkanal of the formula

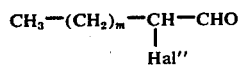

wherein Hal" is a bromine or chlorine and m is 3, 4 or 5 to form a alkyl 3-alkoxy-8-hydroxy-9-halo-6-yne-2-alkenoate of the formula

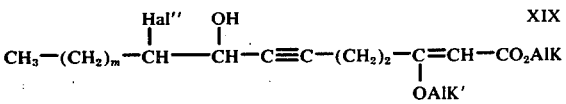

hydroylzing the latter with an acid agent to form alkyl 3-oxo-8-hydroxy-9-halo-6-alkynoate of the formula

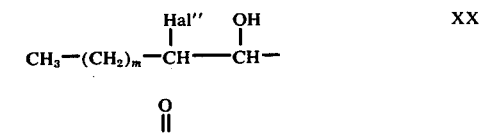

hydrogenating the latter in the presence of a partially deactivated metallic catalyst to form alkyl 3-oxo-8-hydroxy-9-halo-cis-6-alkenoate of the formula

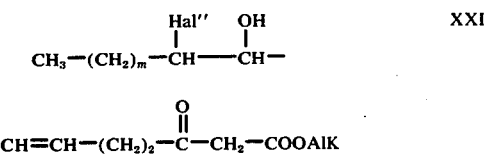

reacting the latter with an alkali metal alcoholate to form a trans epoxy-cis alkene of the formula

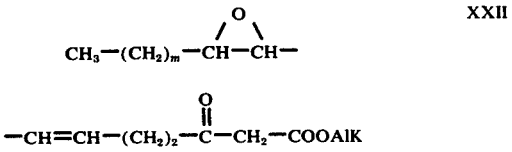

reacting the latter with a secondary amine to form the corresponding enamine which is cyclized in the presence of a basic agent to form alkyl 3-(3'-hydroxy-trans 1'-alkenyl)cyclopentanone-2-carboxylate of the formula

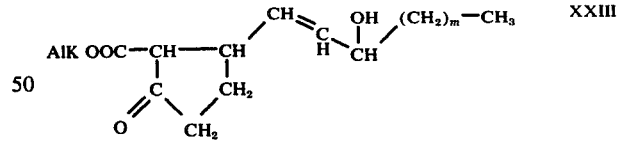

which is etherified by known methods to obtain the corresponding α-tetrahydropyranyl ether.

In a variation of the process of the invention, the compound of formula V is directly bromo-methoxylated and the resulting brominated derivative is dehydrobrominated and the resulting product is subjected to acid hydrolysis to produce the free acid of formula I. This variation has the advantage of eliminating the esterification of the compound of formula V and the final saponification step and this elimination of two steps results in a substantial increase in yield. The said variation may be illustrated by the following reaction scheme.

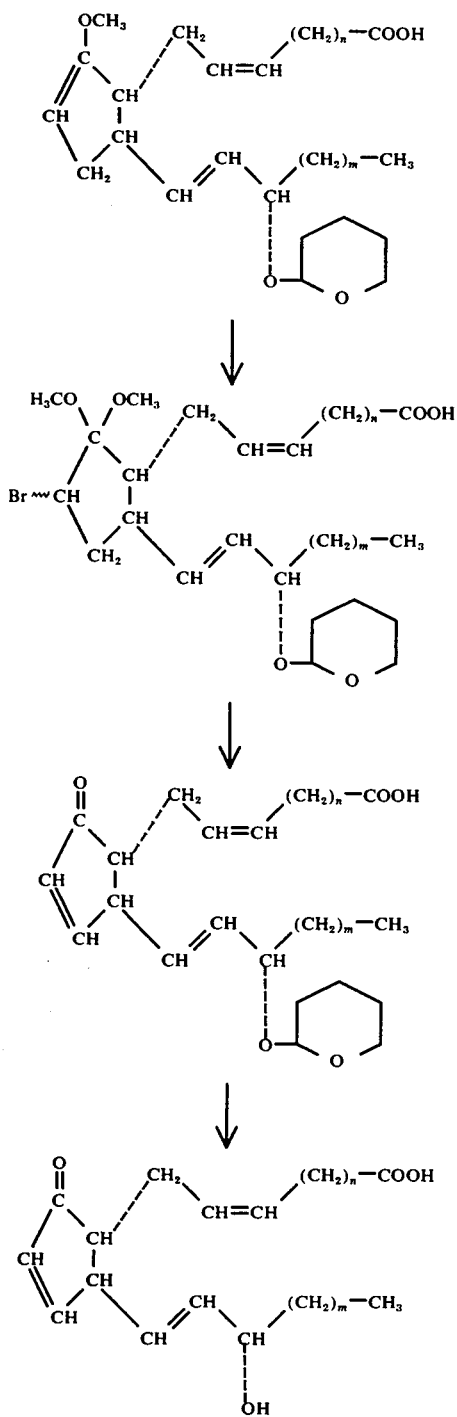

The bromo-methoxylation and dehydrobromination of compounds V and VII', respectively, can be effected as discussed above. While the acid hydrolysis is preferably effected with oxalic acid in ethanol, other acids such as acetic acid, dilute hydrochloric acid and dilute sulfuric acid.

The compound of formula V may be prepared as described above or may be prepared by saponification of the ester of formula VI with an alkaline agent such as sodium hydroxide for a more pure product.

In the following examples there are described several preferred embodiments to illustrate the invention. However, it is to be understood that the invention is not intended to be limited to the specific embodiments.

EXAMPLE I

PREPARATION OF ETHYL 7-bromo-5-heptenoate

STEP A : 6-(α-tetrahydropyranyloxy)-1-chloro 4-hexyne 0.77 g of lithium in the presence of a small amount of ferric nitrate as catalyst was added to 150 cc of ammonia cooled to −35° C and the mixture remained in contact for 1 hour. Then, a solution of 14 g of pyranyl ether of propargyl alcohol [produced by the process of Conia, Bull. Soc. Chim., 1955, p. 1499] in 50 cc of ether were added thereto with stirring which was continued for 2 hours. Then, a solution of 15.7 g of 1-chloro-3-bromo-propane in 25 cc of ether were added thereto and the mixture was stirred for 3 hours at −35° C. The mixture was neutralized by the addition of 5.25 g of ammonium chloride and the ammonia was evaporated off. The residue was treated with ether saturated with water, then with water, and then was extracted with ether. The ether phase was washed with water, dried and evaporated to dryness to obtain 13 g of 6-(α-tetrahydropyranyloxy)-1-chloro-4-hexyne boiling at 100° C at 0.6 mm Hg and having a refractive index $[n]_D^{20} = 1.485$. The product occurred as a colorless liquid soluble in alcohols, ether, benzene and chloroform.

STEP B: 7-(α-tetrahydropyranyloxy)-5-heptyne-nitrile

An aqueous solution of 13.6 g of potassium cyanide was added to 34.174 g of 6-(α-tetrahydropyranyloxy)-1-chloro-4-hexyne in 75 cc of dimethylformamide and the mixture was stirred for 8 hours at 80° C. After cooling, 100 cc of water were added to the reaction mixture which was extracted with ether. The ether phase was washed with water until the wash waters were neutral, dried over magnesium sulfate and evaporated to dryness to obtain 23 g of 7-(α-tetrahydropyranyloxy)-5-heptyne-nitrile boiling at 115° C at 0.1 m Hg and having a refractive index of $[n]_D^{20} = 1.481$. The product occurred as a colorless liquid soluble in alcohols, ether, benzene and chloroform, and insoluble in water.

I R Spectrum

Presence of tetrahydropyranyloxy and CN.

STEP C: 7-(α-tetrahydropyranyloxy)-5-heptynoic acid

A mixture of 22.5 g of 7-(α-tetrahydropyranyloxy)-5-heptyne-nitrile, - 9.5 g of potassium hydroxide and 120 cc of 50% ethanol was heated under a nitrogen atmosphere with stirring at 80° C for 18 hours and then the ethanol was removed under reduced pressure. 50 cc of water were added to the mixture which was iced and after the addition of 150 cc of ether, the pH was adjusted to 4 by addition of iced 0.5N hydrochloric acid. The ether phase was washed with water, dried over magnesium sulfate, filtered and evaporated to dryness under reduced pressure to obtain 21.3 g of 7-(α-tetrahydropyranyloxy)-s-heptynoic acid in the form of a colorless liquid having a refractive index $[n]_D^{20} = 1.485$. The liquid was soluble in alcohols, ether, benzene and chloroform and insoluble in water.

STEP D: ETHYL 7-(α-tetrahydropyranyloxy)-5-heptynoate

A mixture of 20 g of 7-(α-tetrahydropyranyloxy)-5-heptynoic acid, 100 cc of methanol and 5.4 g of sodium methylate was stirred at room temperature for 1 hour and the methanol was evaporated off under reduced pressure to obtain 22 g of sodium 7-(α-tetrahydropyranyloxy)-5-heptynoate. 21 g of said sodium salt and 70cc of dimethylformamide were mixed, then 27.2 g of ethyl bromide were added thereto. The reaction mixture was heated at 80° C for 2 hours with stirring and was then poured into water. The mixture was extracted with ether and the ether phase was washed with water, dried over magnesium sulfate and the solvent was evaporated off. The residue was fractionated to obtain 13 g of ethyl 7-(α-tetrahydropyranyloxy)-5-heptynoate boiling at 122° C at 0.1 mm Hg and having a refractive index $[n]_D^{20} = 1.47$. The colorless liquid was soluble in alcohol, ether, benzene and chloroform and insoluble in water.

STEP E: ETHYL 7-hydroxy-5-heptynoate

A mixture of 10 g of ethyl 7-(α-tetrahydropyranyloxy)-5-heptynoate, 20 cc of ether, 5 cc of 25% sulfuric acid and 20 cc of methanol was stirred for 1 hour and then 30 cc of water were added thereto. The mixture was extracted with ether and the ether extracts were washed with water, dried over sodium carbonate and the ether was evaporated off under reduced pressure to obtain 4.3 g of ethyl 7-hydroxy-5-heptynoate boiling at 91° C at 0.5 mm Hg and having a refractive index $[n]_D^{20} = 1.465$. The colorless liquid was soluble in alcohols, ether, benzene and chloroform and insoluble in water.

STEP F: ETHYL 7-hydroxy-5-heptenoate

A mixture of 300 mg of 5% palladium over barium sulfate in 20 cc of ethyl acetate was purged and a current of hydrogen was passed therethrough until 6 cc of hydrogen were absorbed. A solution of 4 g of ethyl 7-hydroxy-5-heptynoate in 7 cc of ethyl acetate containing 0.4 cc of quinolin was added thereto and the mixture was washed with 14 cc of ethyl acetate. The mixture was purged and the current of hydrogen was passed therethrough until 570 cc of hydrogen were absorped and the mixture was filtered and the filter was washed with ethyl acetate. The organic phase was washed with 0.5N hydrochloric acid, then with water, dried over magnesium sulfate, treated with activated carbon, filtered and evaporated to dryness to obtain 2.6 g of ethyl 7-hydroxy-5-heptenoate. The product occurred as a colorless liquid having a refractive index $[n]_D^{20} = 1.453$ and soluble in alcohols, ether, benzene and chloroform and insoluble in water.

STEP G: ETHYL 7-bromo-5-heptenoate

A solution of 2.9 g of phosphorus tribromide in 30 cc of petroleum ether was added with agitation at −10° C to a mixture of 10 g of ethyl 7-hydroxy-5-heptenoate and 120 cc of petroleum ether, and the mixture was stirred for 30 minutes at −10° C and 1 hour at 0° C. The reaction mixture was added to water and the mixture was extracted with ether. The ether extracts were washed with water until the wash waters were neutral, dried over magnesium sulfate and evaporated to dryness under reduced pressure to obtain 11.55 g of an oily product. The product was purified by passage through silica gel and elution with an 85–15 mixture of cyclohexane-ethyl acetate to obtain 9.73 g of ethyl 7-bromo-5-heptnoate in the form of a colorless liquid with a refractive index $[n]_D^{20} = 1.4825$. The product was soluble in alcohols, ether, benzene and chloroform and insoluble water.

EXAMPLE II

PREPARATION of Ethyl 3-(3'α-tetrahydropyranyloxy trans-1'-octenyl)-cyclopentanone-2-carboxylate

STEP A: Ethyl 3-oxo-6-heptynoate 7.3g of mono ethyl malonate (Bram et al, Bull. Soc. Chim., 1964, p. 945) were dissolved under a nitrogen atmosphere in 50 cc of tetrahydrofuran and then 0.10 mol of isopropyl magnesium bromide in solution in tetrahydrofuran was added. The mixture was heated slightly and allowed to return to room temperature while maintaining the nitrogen atmosphere to form solution A.

15 g of imidazole were dissolved in 100 cc of tetrahydrofuran and a solution of 6 g of thionyl chloride in 30 cc of tetrahydrofuran was added thereto. After stirring for 15 minutes, the mixture was filtered and the filter was washed with tetrahydrofuran to obtain a solution of N,N'-thionyldimidazole, 5 g of propargylacetic acid dissolved in 50 cc of tetrahydrofuran was added to the said solution and the mixture was stirred for 15 minutes at room temperature to obtain a solution of propargylacetylimidazole which was used as is.

Solution A was added to the solution of propargylacetylimidazole and the mixture was stirred overnight at room temperature. The mixture was acidified by addition of 4% hydrochloric acid and was extracted with ether. The ether phase was washed with an aqueous sodium bicarbonate solution, dried, treated with activated carbon, filtered and evaporated to dryness. The residue was passed through alumina with elution with methylene chloride to obtain 6.03 g of ethyl 3-oxo-6-heptynoate which was used as is for the next step.

The product occurred in the form of pale yellow prisms melting at 25° C and soluble in alcohols, ether, benzene and chloroform and insoluble in water.

STEP B: Ethyl 3-ethoxy-6-yne-2-heptenoate 30 cc of ethyl orthogormate and 0.35 cc of concentrated sulfuric acid were added to a solution of 10 g of ethyl 3-oxo-6-heptynoate in 60 cc of ethanol and 25 cc of solvent were distilled off in 45 minutes while bubbling nitrogen therethrough. After cooling the mixture, methylene chloride was added thereto and the mixture was washed with 2N sodium hydroxide. The mixture was extracted with methylene chloride and the organic phases were dried over sodium sulfate, treated with activated carbon, filtered and evaporated to dryness under reduced pressure. The residue was chromatographed over silica gel and elution with methylene chloride to obtain 7.05 g of ethyl 3-ethoxy-6-yne-2-heptenoate. The product occurred in the form of a pale yellow liquid soluble in alcohols, ether, benzene and chloroform and insoluble in water.

STEP C: Ethyl 3-ethoxy-8-hydroxy-9-chloro-6-yne-2-tetradecenoate 9.25 cc of an ether solution of 1.085 N butyllithium were added to a mixture of 2 g of ethyl 3-ethoxy-6-yne-2-heptenoate and 15 cc of tetrahydrofuran cooled to −25° C and the mixture was left standing at −25° C for 1½ hours. After cooling the mixture to −30° C, 3 g of α-chloroheptanal (process of Krattiger, Bull. Soc. Chim., 1953, p. 222) were added thereto and the mixture stood for 30 minutes at −20° C, at 0° C for 30 minutes and then returned to room temperature. The reaction mixture was added to an iced aqueous solution of monosodium phosphate and was extracted with ether. The organic phae was washed with aqueous sodium bicarbonate solution, then water and finally with aqueous sodium chloride solution. The solution was dried over sodium sulfate, treated with activated carbon, filtered and evaporated to dryness. The residue was chromatographed over silica gel with elution with methylene chloride containing 0.5% of acetone. The residue was purified by another chromatography over silica gel with elution with methylene chloride containing 0.25% of acetone and then 0.5% acetone to obtain 1.85 g of ethyl 3-ethoxy-8-hydroxy-9-chloro-6-yne-2-tetradecenoate in the form of an amorphous pale yellow product soluble in alcohols and ether and insoluble in water.

Analysis: $C_{18}H_{29}O_4Cl$; molecular weight = 344.87
Calculated: % Cl  10.28
Found:                10.3
U. V. Spectrum (ethanol):

Max. at 237 nm      $E_{1\,cm}^{1\%}$ = 357

STEP D: Ethyl 3-oxo-8-hydroxy-9-chloro-6-tetradecynoate

A mixture of 6.95 g of ethyl 3-ethoxy-8-hydroxy-9-chloro-6-yne-2-tetradecenoate, 70 cc of ethanol and 35 cc of 2N hydrochloric acid was heated with stirring under a nitrogen atmosphere at 50° C for 1½ hours, and after cooling, the reaction mixture was poured into water, and was extracted with methylene chloride. The organic phase was washed with an aqueous sodium bicarbonate solution and then water until the washed waters were neutral, dried over sodium sulfate, filtered and evaporated to dryness under reduced pressure to obtain 6 g of raw ethyl 3-oxo-8-hydroxy-9-chloro-6-tetradecynoate. The product was purified by chromatography over silica gel and elution with a 70–30 mixture of cyclohexane-ethyl acetate to obtain pale yellow crystals soluble in alcohols and ether and insoluble in water.

Analysis: $C_{16}H_{25}O_4Cl$; molecular weight = 316.82
Calculated: % Cl  11.2
Found:                11.4
U. V. Spectrum:

Ethanol    max. at 244 nm      $E_{1\,cm}^{1\%}$ = 34 infl. towards 279 nm  $E_{1\,cm}^{1\%}$ = 6

Ethanol - 0.1N NaOH

Max. at 275 nm      $E_{1\,cm}^{1\%}$ = 668

STEP E: Ethyl 3-oxo-8-hydroxy-9-chloro-cis-6-tetradecenoate 240 mg of 5% palladium on barium sulfate were added to 15 cc of ethylacetate and a current of hydrogen was passed therethrough for 30 minutes. After absorption of 6 cc of hydrogen, a solution of 3.03 g of ethyl 3-oxo-8-hydroxy-9-chloro-6-tetradecynoate in 5 cc of ethyl acetate containing 0.3 cc of quinoline was added thereto and the mixture was washed with 15 cc of ethyl acetate. The current of hydrogen was passed through the mixture for 2 hours and after absorption of 223 cc of hydrogen, the mixture was filtered. The filter was washed with ethyl acetate and the organic phase was washed with 0.5N hydrochloric acid, then with water and was dried over sodium sulfate, treated with activated carbon and filtered. The filtrate was evaporated to dryness under reduced pressure to obtain 3 g of ethyl 3-oxo-8-hydroxy-9-chloro-cis-6-tetradecenoate in the form of an amorphous, pale yellow product soluble in alcohols and ether and insoluble in water.

Analysis: $C_{16}H_{27}O_4Cl$; molecular weight = 318.84
Calculated:  % C  60.27    % H  8.54    % Cl  11.12
Found:             60.0             8.4           10.8
U. V. Spectrum (ethanol):

Inflex. towards 226 nm    $E_{1\,cm}^{1\%}$ = 25

Max. at 243 nm              $E_{1\,cm}^{1\%}$ = 32

STEP F: Ethyl 3-oxo-trans-8,9-epoxy-cis-6-tetradecenoate 32 cc of a solution of 1N potassium tertiary butylate in tertiary butanol were added under nitrogen while stirring for 45 minutes to a solution of 5 g of ethyl 3-oxo 8-hydroxy 9-chloro cis 6-tetradecenoate in 50 cc of tertiary butanol. Methylene chloride was added thereto and the mixture was poured into a saturated aqueous solution of monosodium phosphate. The mixture was extracted with methylene chloride and the organic phase was washed with water, dried over sodium sulfate, treated with activated carbon, filtered and evaporated to dryness under reduced pressure. The residue was chromatographed over silica gel with elution with a 1:1 mixture of cyclohexane and ethyl acetate to obtain 3.4 g of ethyl 3-oxo-trans-8,9-epoxy-cis-6-tetradecenoate in the form of a pale yellow liquid, soluble in most of the usual organic solvents and insoluble in water.

Analysis: $C_{16}H_{26}O_4$; molecular weight = 282.38
Calculated:  % C  68.05    % H  9.28
Found:             68.3             9.4
U. V. Spectrum (ethanol):

Max. at 246 nm      $E_{1\,cm}^{1\%}$ = 49

STEP G: Ethyl 3-N-pyrrolidyl-trans 8,9-epoxy-2-cis-6-tetradecadienoate

A mixture of 1.5 g of ethyl 3-oxo-trans-8,9-epoxy-cis-6-tetradecenoate, 15 cc of benzene, 1.5 cc of pyrrolidine and 75 mg of p-toluene sulfonic acid was purged with nitrogen and was then stirred at room temperature for 4 days. At the end of this time, the mixture was evaporated to dryness under reduced pressure and toluene was added to eliminate excess pyrrolidine. The residue was dissolved in methylene chloride and the organic phase was washed with water. The wash waters were re-extracted with methylene chloride and the combined methylene chloride phases were dried over magnesium sulfate, treated with activated carbon, filtered and evaporated to dryness under reduced pressure to obtain 1.9 g of ethyl 3-N-pyrrolidyl-trans 8,9-epoxy-2-cis 6-tetradecadienoate in the form of dark yellow amorphous solid soluble in alcohols and chloroform and insoluble in water.

Analysis: $C_{20}H_{33}O_3N$; molecular weight = 335.47
Calculated:    % N  4.17
Found:              4.9
U. V. Spectrum (ethanol):
Inflex. towards 230 nm    $E_{1cm}^{1\%} = 70$
Max. at 289-290 nm    $E_{1cm}^{1\%} = 740$
I.R. Spectrum:
Absence of OH and bands of 1671, 1565, 1446 and 1143 $cm^{-1}$.

STEP H: Ethyl 3-(3'-hydroxy-trans 1'-octenyl)-cyclopentanone-2-carboxylate 4.3 g of sodium amide were added under nitrogen to 9.3 g of ethyl 3-N-pyrrolidyl-trans 8,9-epoxy-2 cis 6-tetradecadienaoate in 110 cc of tetrahydrofuran and the mixture was stirred overnight at room temperature. The mixture was poured into an iced aqueous solution of monosodium phosphate and the mixture was extracted with methylene chloride. The organic phase was washed with water, dried over magnesium sulfate, treated with activated carbon, filtered and evaporated to dryness under reduced pressure. The residue was chromatographed over silica gel to obtain 3.4 g of ethyl 3-(3'-hydroxy-trans 1'-octenyl)-cyclopentanone-2-carboxylate in the form of a yellow liquid soluble in alcohols, ether, benzene and chloroform and insoluble in water.

Analysis: $C_{23}H_{28}O_9N_2$; molecular weight = 476.47 (dinitrobenzoate)
Calculated:    % C 57.98    % H 5.88    % N 5.88
Found:              57.8             6.0             6.1

STEP I: Ethyl 3-(3'-α-tetrahydropyranyloxy-trans 1'-octenyl)-cyclopentanone-2-carboxylate 4 crystals of p-toluene sulfonic acid and then 4 cc of dihydropyran were added to a solution of 3 g of ethyl 3-(3'-hydroxy-trans 1'-octenyl)-cyclopentanone-2-carboxylate in 10 cc of ether cooled to 0° C and the mixture was allowed to return to room temperature. The mixture was added to anhydrous sodium carbonate and was stirred for 1 hour under nitrogen. After filtration, the solvent and excess dihydropyran was evaporated off under reduced pressure to obtain 3.89 g of ethyl 3-(3'-α-tetrahydropyranyloxy-trans 1'-octenyl)-cyclopentanone-2-carboxylate in the form of a colorless liquid soluble in alcohols, ether and chloroform and insoluble in water.

Analysis: $C_{21}H_{34}O_5$: molecular weight = 366
Calculated:    % C 68.85    % H 9.29
Found:              68.9             9.0

EXAMPLE III

PREPARATION OF ETHYL 15α-(α-tetrahydropyranyloxy)-10-carbethoxy-9-oxo-5-cis 13-trans Prostadienoate

STEP A: ETHYL 15α-(α-tetrahydropyranyloxy)-9-oxo-8-carbethoxy-5-cis 13-trans Prostadienoate A solution of 3.3 g of ethyl 3-(3'α-tetrahydropyranyloxytrans 1'-octenyl)-cyclopentanone-2-carboxylate in 15 cc of benzene was admixed with 1.165 g of potassium tertbutylate under a nitrogen atmosphere with stirring at room temperature for 1 hour and then a solution of 2.76 g of ethyl 7-bromo-5-heptenoate in 5 cc of benzene was added to the reaction mixture which was allowed to stand at room temperature for 24 hours. The reaction mixture was poured into an aqueous solution of iced monosodium phosphate and the mixture was extracted with methylene chloride. The organic phase was washed with water until the wash water was neutral and the wash waters were reextracted with methylene chloride. The combined organic phases were dried over magnesium sulfate and evaporated to dryness. The residue was chromatographed through silica gel and eluted with a 80–20 mixture of cyclohexane-ethyl acetate to obtain 3.9 g of ethyl 15α-(α-tetrahydropyranyloxy)-9-oxo-8-carbethoxy-5-cis 13-trans prostadienoate in the form of a colorless liquid soluble in organic solvents and insoluble in water.

Analysis: $C_{30}H_{48}O_7$; molecular weight = 520
Calculated:    % C 69.23    % H 9.23
Found:              68.9             9.2
I.R. Spectrum
Presence of carbonyl at 1727 and 1746 $cm^{-1}$

STEP B: ETHYL 15α-(α-tetrahydropyranyloxy)-10-carbethoxy-9-oxo-5-cis 13-trans prostadienoate A mixture of 2.8 g of ethyl 15α-(α-tetrahydropyranyloxy)-9-oxo-8-carbethoxy-5-cis 13-trans-prostadienoate and 5.6 cc of an alcoholic solution of 1.02 N sodium ethylate was refluxed for 7 hours and after cooling, 20 cc of toluen were added thereto. The alcohol was azeotropically distilled off at the attained temperature of 110° C. The reaction mixture was strongly cooled and then was poured into an aqueous solution of monosodium phosphate with agitation. The mixture was extracted with ether and the organic phase was washed with water, dried over magnesium sulfate and the solvent was evaporated off under reduced pressure. The residue was chromatographed over silica gel and eluted with a 90–10 mixture of cyclohexaneethyl acetate containing 0.1% triethylamine to obtain 2.3 g of ethyl 15α-(α-tetrahydropyranyloxy)-10-carbethoxy-9-oxo-5-cis 13-trans prostadienoate in the form of a colorless liquid soluble in organic solvents and insoluble in water.

Analysis: $C_{30}H_{48}O_7$; molecular weight = 520
Calculated:    % C 69.23    % H 9.23
Found:              69.4             8.9

EXAMPLE IV

PREPARATION OF METHYL 15α-HYDROXY-9-OXO-5-CIS 10,13-TRANS PROSTATRIENOATE

STEP A: ETHYL 15α-(α-tetrahydropyranyloxy)-10-carbethoxy-9-methoxy-5-cis 9,13-trans-prostatrienoate 420 mg of ethyl 15α-(α-tetrahydropyranyloxy)-10-carbethoxy-9-oxo-5-cis 13-trans prostadienoate were dissolved in 10 cc of ether and then 40 cc of a methylene chloride solution of diazomethane titrating 1.5 g per 100 cc were added at 0° C and stirred. The reaction mixture was permitted to return to room temperature and agitation was continued for 8 hours. Excess diazomethane was then evaporated under reduced pressure at a temperature below 40° C. The reaction mixture was extracted with ether, dried over magnesium sulfate and evaporated to dryness. The residue was chromatographed over silica gel and eluted with a mixture to cyclohexane-ethyl acetate-triethylamine (80-20-0.3). Evaporation of the eluate resulted in 295 mg of ethyl 15α-(α-tetrahydropyranyloxy)-10-carbethoxy-9-methoxy-5-cis, 9,13-trans prostatrienoate in the form of a clear yellow liquid soluble in most organic solvents and insoluble in water.

Analysis: $C_{31}H_{50}O_7$; molecular weight = 534
Calculated: % C 68.5  % H 9.4
Found: 68.3  9.0
I. R. Spectrum (chloroform):
Presence of non-conjugated ester at 1729$^{cm-1}$, of conjugated ester at 1693$^{cm-1}$, of conjugated C=C at 1627$^{cm-1}$ and of C-O-C.
U. V. Spectrum:
Max. at 254 nm  $\epsilon = 10,600$ As far as is known, this compound is not described in the literature.

STEP B: 15α-(α-tetrahydropyranyloxy)-10-carboxy-9-methoxy-5-cis, 9,13-trans prostatrienoic acid 190 mg of ethyl 15α-(α-tetrahydropyranyloxy)-10-carbethoxy-9-methoxy-5-cis, 9,13-trans-prostatrienoate, 1.065 cc of N sodium hydroxide and 1 cc of a 1-1 dioxane-methanol mixture were heated at 70° C for 6 hours and the solvent was then distilled off at reduced pressure at a temperature below 40° C. 3 cc of water were added thereto and the mixture was extracted with ether to remove the neutral fractions. The aqueous solution was cooled, saturated with sodium chloride and acidified with 1N aqueous hydrochloric acid. The aqueous phase was extracted with ether and the ether extracts were washed with water until the wash waters were neutral, were dried over magnesium sulfate and then distilled to dryness under reduced pressure to obtain 170 mg of 15α-(α-tetrahydropyranyloxy)-10-carboxy-9-methoxy-5-cis, 9,13-trans prostatrienoic acid in the form of a pale yellow liquid soluble in most organic solvents and insoluble in water.

Analysis: $C_{27}H_{42}O_7$; molecular weight = 478
Calculated: % C 65.38  % H 8.94
Found: 65.7  8.8
I. R. Spectrum (chloroform):
Presence of -C-O-C-, of acid, complexed C=O at 1726 and 1713$^{cm-1}$ and complexed C=C at 1634 and 1615$^{cm-1}$.
U. V. Spectrum
Max. at 250 nm  $\epsilon = 8,950$ As far as is known, this compound is not described in the literature.

STEP C: Methyl 9-methoxy-15α-(α-tetrahydropyranyloxy)-5-cis, 9,13-trans prostatrienoate A mixture of 478 mg of 15α-(α-tetrahydropyranyloxy)-10-carboxy-9-methoxy-5-cis, 9,13-trans prostatrienoic acid and 12 cc of xylene were refluxed for 3 hours and then the xylene was distilled off under reduced pressure at a temperature below 60° C to obtain 15α-(α-tetrahydropyranyloxy)-9-methoxy-5-cis, 9,13-trans-prostatrienoic acid. The said acid was purified by chromatography over silica gel with elution with ethyl acetate. The residue was taken up in ether and a solution of diazomethane in methylene chloride titrating 1.5 g per 100 cc. was added at 0° C. The solvent was evaporated off at reduced pressure and the residue was chromatographed over silica gel and eluted with a 90-10-1 mixture of cyclohexane-ethyl acetate-triethylamine. The eluant was evaporated off to obtain 125 mg of methyl 15α-(α-tetrahydropyranyloxy)-9-methoxy-5-cis, 9,13-trans prostatrienoate in the form of a clear yellow liquid soluble in most organic solvents and insoluble in water.

Analysis: $C_{27}H_{44}O_5$; molecular weight = 448
Calculated: % C 72.38  % H 9.9
Found: 72.2  10.1
Saponification indice:  calculated 125 – Found 125
I.R. Spectrum (chloroform):
 cm-1
Presence of C=C at 1645 $cm-1$ and C=O of an ester As far as is known, this compound is not described in the literature.

STEP D: METHYL 15α-(α-tetrahydropyranyloxy)-10ξ-bromo-9,9-dimethoxy-5-cis, 13-trans prostadienoate A mixture of 836 mg of methyl 15α-(α-tetrahydropyranyloxy)-9-methoxy-5 cis, 9,13-trans prostatrienoate, 50 cc of methanol and 690 mg of sodium acetate was cooled to −60° C and then 9.5 cc of a methanolic solution of bromine (titrating 3.3 gm per 100 cc) had added. The reaction mixture was allowed to return to room temperature, and after 500 mg of sodium bicarbonate were added thereto, the mixture was left for 1 hour at room temperature. The mixture was evaporated to dryness at reduced pressure, and the residue was taken up in a ether/water mixture (3 : 1). The ether phases were washed with water until the wash water was neutral, dried over magnesium sulfate and sodium bicarbonate and filtered. 2 to 3 drops of triethylamine were added to the ether solution and the solvent was evaporated under reduced pressure to obtain 1 gm of methyl 15α-(α-tetrahydropyranyloxy)-10ξ-bromo-9,9-dimethoxy-5 cis, 13-trans prostadienoate which was used as is in the following step.

As far as is known, this compound has not been described in the literature.

STEP E: METHYL 15α-(α-tetrahydropyranyloxy)-9-oxo-5 cis, 10,13-trans prostatrienoate A mixture of 1 gm of methyl 10ξ-bromo-15α-(α-tetrahydropyranyloxy)-9,9-dimethoxy-5-cis, 13-trans prostadienoate, 15 cc of dimethylsulfoxide and 1.15 gm of 1,5-diaza-bicyclo(4-3-O) nonene-5 was heated at 85° C for 15 hours and then the dimethylsulfoxide and the 1,5-diaza-bicyclo (4-3-O) nonene-5 were distilled off at 80° C at a pressure of 0.5 mm of mercury. The residue was taken up in ethyl acetate, and the solution was poured into a saturated solution of monosodium phosphate and agitated for 15 minutes. The mixture was decanted and the organic phases were washed with water, while the aqueous phases were extracted with methylene chloride. The combined organic phases were dried over magnesium sulfate and evaporated to dryness. The residue was chromatographed over silica gel and eluted with a cyclohexane/ethyl acetate mixture (70:30). Evaporation of the eluent gave 380 mg of methyl 15α-(α-tetrahydropyranyloxy)-9-oxo-5-cis, 10,13-trans prostatrienoate as a yellow oil, soluble in most organic solvents and insoluble in water.

Analysis: $C_{26}H_{40}O_5$; molecular weight = 432
Calculated: % C 72.22 % H 9.25
Found: 72.5 9.3
I.R. Spectrum (chloroform):
Presence of C=O ester at $1730^{cm-1}$, of C=O cyclopentanone at $1705^{cm-1}$ and of C=C at $1588^{cm-1}$
U. V. Spectrum (ethanol):
Max. at 217 nm $\epsilon = 10\ 050$ As far as is known, this compound has not been described in the literature.

STEP F: METHYL 15α-hydroxy-9-oxo-5-cis, 10,13-trans prostatrienoate

A mixture of 360 mg of methyl 15α-(α-tetrahydropyranyloxy)-9-oxo-5-cis, 10,13-trans prostatrienoate, 10 cc of methanol, 21 mg of oxalic acid. $2H_2O$ and 1 cc of water was heated with agitation at 45° C for 8 hours. Then the solvents were evaporated off under reduced pressure, and the residue was taken up in chloroform. The chloroform phase was washed with water until the wash water was neutral, dried over magnesium sulfate and evaporated to dryness. The residue was chromatographed over silica gel and eluted with a cyclohexane/ethyl acetate mixture (50:50). Evaporation of the eluant gave 220 mg of methyl 15-α-hydroxy-9-oxo-5-cis, 10,13-trans prostatrienoate as a colorless liquid, soluble in most organic solvents and insoluble in water.

Analysis: $C_{21}H_{32}O_4$; molecular weight = 348
Calculated: % C 72.37 % H 9.26
Found: 72.7 9.4
U. V. Spectrum (ethanol):
Max. at 216 nm $\epsilon = 10\ 100$

EXAMPLE V

15α-hydroxy-9-oxo-5-cis, 10,13-trans prostatrienoic acid

STEP A:
15α-(α-tetrahydropyranyloxy)-9-methoxy-5-cis, 9,13-trans prostatrienoic acid A mixture of 2.6 gm of methyl 15α-(α-tetrahydropyranyloxy)-9-methoxy-5-cis, 9,13-trans prostatrienoate, 8.7 cc of N sodium hydroxide, 20 cc of methanol and 5 cc of dioxane was heated at 40° C for 5 hours and the methanol was then evaporated off. The reaction mixture was extracted with diethyl ether and then previously iced aqueous phase was acidified with N hydrochloric acid and extracted with ethyl acetate. The organic phase was dried over magnesium sulfate and, after the evaporation of the solvent, 2.45 gm of 15α-(α-tetrahydropyranyloxy)-9-methoxy-5-cis, 9,13-trans prostatrienoic acid were obtained.

STEP B:
15α-(α-tetrahydropyranyloxy)-10ξ-bromo-9,9-dimethyloxy-5-cis, 13-trans prostadienoic acid 2.45 gm of 15α(α-tetrahydropyranyloxy)-9-methoxy-5-cis, 9,13-trans prostatrienoic acid, obtained as described in step C of example IV, 200 cc of methanol and 2.13 gm of sodium acetate were cooled to −70° C, then dropwise 18.5 cc of a methanol solution of bromine, titrating 5.5 gm in 100 cc were added over an hour. The reaction mixture was allowed to return to room temperature and was agitated for 1 hour. The mixture was then evaporated to dryness at reduced pressure, and the residue was take up in a ether/ethyl acetate mixture (1:1). The solution was dried and a few drops of 1,5-diaza-bicyclo (4-3-0) nonene-5 were added just to an alkaline reaction, and then the mixture was evaporated to dryness to obtain 3.16 gm of 15α-(α-tetrahydropyranyloxy)-10ξ-bromo-9,9-dimethoxy-5-cis, 13-trans prostadienoic acid as a yellow oil.

As far as is known, this compound has not been described in the literature.

STEP C: 15α-(α-tetrahydropyranyloxy)-9-oxo-5-cis, 10,13-transprostatrienoic acid A mixture of 3.16 gm of 10ξ-bromo-15α-(α-tetrahydropyranyloxy)-9,9-dimethoxy-5-cis, 13-trans prostadienoic acid, 50 cc of dimethylsulfoxide and 4.5 gm of 1,5-diaza-bicyclo (4-3-0) nonene-5 was heated for 15 hours at 80° C and then the dimethylsulfoxide and the 1,5-diazo-bicyclo (4-3-0) nonene-5 were distilled off at 80° C at a pressure of 0.1 mm of mercury. The residue was taken up in ethyl acetate, and the solution was poured into a saturated solution of monosodium phosphate and agitated for 1 hour. The mixture was decanted, and the organic phase was dried over magnesium sulfate and evaporated to dryness to obtain 2.1 gm of 15α-(α-tetrahydropyranyloxy)-9-oxo-5-cis, 10,13-trans prostatrienoic acid as a yellow oil.

As far as known, this compound has not been described in the literature.

STEP D: 15α-hydroxy-9-oxo-5-cis, 10,13-trans prostatrienoic acid

A mixture of 2.1 gm of 15α-(α-tetrahydropyranyloxy)-9-oxo-5-cis, 10,13-trans prostatrienoic acid, 60 cc of methanol and 126 mg of oxalic acid was heated at 40° C with agitation for 3 hours, and the solvent was then evaporated off under reduced pressure. The residue was taken up in chloroform, and the chloroform phase washed with water until the wash water was neutral, dried over magnesium sulfate and evaporated to dryness at reduced pressure to obtain 1.65 gm of 15α-hydroxy-9-oxo-5-cis, 10,13-trans prostatrienoic acid as an oil.

This compound was identical with that described by S. E. PIKE et al. p:164 Nobel Symposium Stockholm, June 1966 (prostaglandins), published by Sune Bergstrom and B. Samnelson, published by Interscience Publishers, New York, London, Sydney.

Various modification of the products and process of the invention may be made without departing from the spirit or scope thereof and it is to be understood that the invention is to be limited only as defined in the appended claims.

We claim:

1. A process for the preparation of an ester compound of the formula

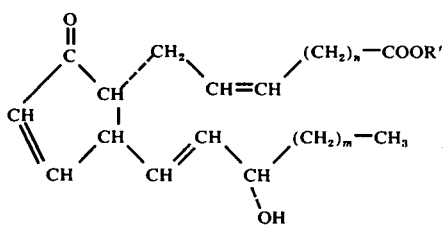

wherein R' is lower alkyl, n is 2, 3 or 4 and m is 3, 4 or 5 comprising reacting a compound of the formula

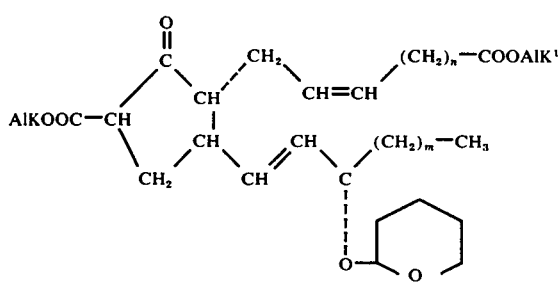

wherein Alk and Alk¹ are lower alkyl with a methylating agent to form a compound of the formula

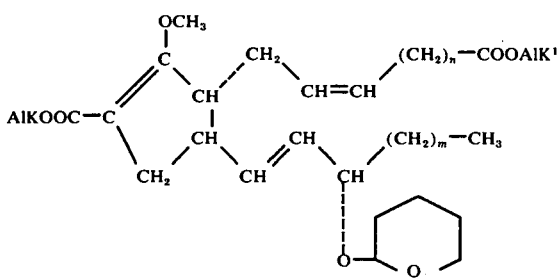

saponifying the said compound with a basic agent to form a compound of the formula

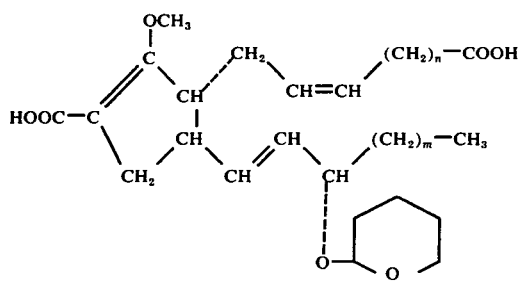

heating the said compound 50° to 120° C to form a compound of the formula

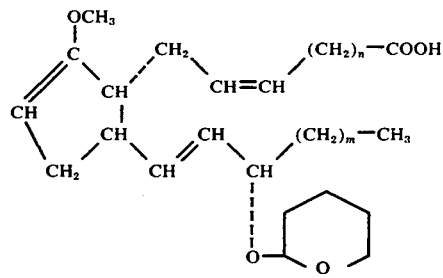

reacting the latter with an esterification agent to obtain an ester of the formula

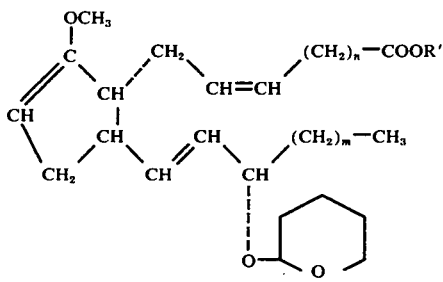

wherein R' is lower alkyl, reacting the latter under mild selective conditions with bromine in methanol at −30° to −70° C to form a bromo ketal of the formula

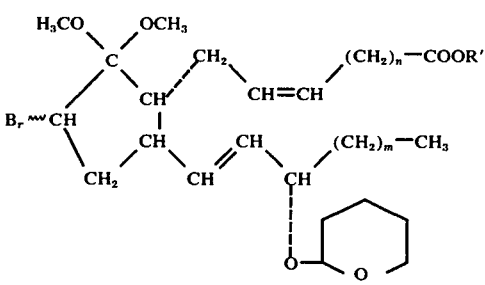

dehydrobrominating the latter with a diazabicycloalkene dehydrobromination agent to form a compound of the formula

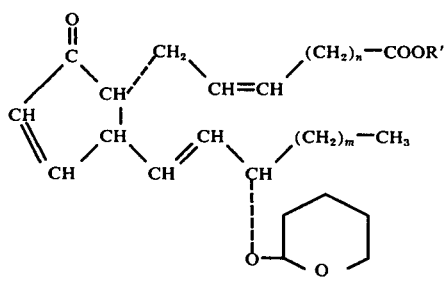

and subjecting the latter to said hydrolysis to form the said ester.

2. The process of claim 1 wherein the ester compound is saponified with a mildly basic agent to form the corresponding free acid.

3. The process of claim 1 wherein the saponification is effected below 50° C.

4. The process of claim 1 wherein heating step is effected in an anhydrous organic solvent.

5. The process of claim 1 wherein the dehydrobromination agent is 1,5-diazabicyclo[4-3-0]nonene-5 and the reaction is effected a dipolar aprotic solvent.

6. The process of claim 1 wherein the acid hydrolysis is effected with oxalic acid.

7. A process for the preparation of a compound of the formula

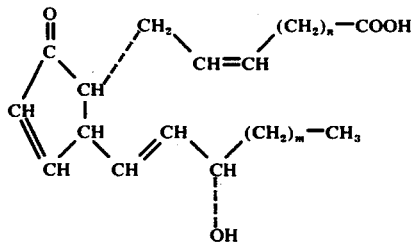

wherein n is 2, 3 or 4 and m is 3, 4 or 5 comprising reacting a compound of the formula

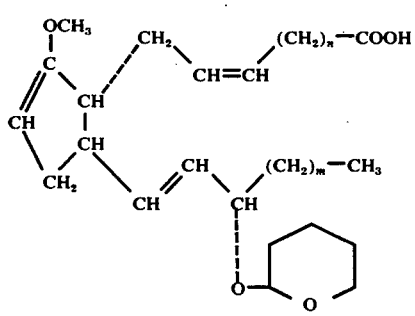

with bromine in methanol at −30 to −70° C under mild selective conditions to form a bromo compound of the formula

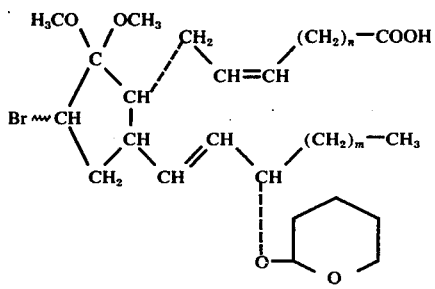

dehydrobrominating the latter with a diazabicycloalkene to form a compound of the formula

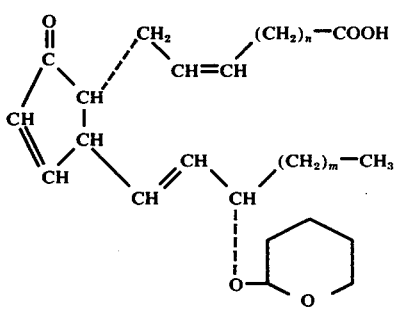

and subjecting the latter to acid hydrolysis to obtain the desired acid compound.

* * * * *